(12) United States Patent
Ishii et al.

(10) Patent No.: US 7,393,979 B2
(45) Date of Patent: Jul. 1, 2008

(54) PROCESS FOR PRODUCING OPTICALLY ACTIVE 1-ALKYL-SUBSTITUTED 2,2,2-TRIFLUOROETHYLAMINE

(75) Inventors: Akihiro Ishii, Saitama (JP); Yokusu Kuriyama, Niiza (JP); Manabu Yasumoto, Kamifukuoka (JP); Masatomi Kanai, Shiki (JP); Kenjin Inomiya, Kamifukuoka (JP); Takashi Ootsuka, Kamifukuoka (JP); Koji Ueda, Kamifukuoka (JP)

(73) Assignee: Central Glass Company, Limited, Ube-shi (JP)

( * ) Notice: Subject to any disclaimer, the term of this patent is extended or adjusted under 35 U.S.C. 154(b) by 53 days.

(21) Appl. No.: 10/560,251

(22) PCT Filed: Jun. 8, 2004

(86) PCT No.: PCT/JP2004/007955

§ 371 (c)(1),
(2), (4) Date: May 16, 2006

(87) PCT Pub. No.: WO2004/110977

PCT Pub. Date: Dec. 23, 2004

(65) Prior Publication Data

US 2006/0281950 A1 Dec. 14, 2006

(30) Foreign Application Priority Data

Jun. 11, 2003 (JP) ............................. 2003-166525

(51) Int. Cl.
*C07C 209/62* (2006.01)
*C07C 211/05* (2006.01)

(52) U.S. Cl. ...................... 564/486; 564/392
(58) Field of Classification Search ........................ None
See application file for complete search history.

(56) References Cited

U.S. PATENT DOCUMENTS 5,939,588 A 8/1999 Soloshonok et al.

FOREIGN PATENT DOCUMENTS

JP 10-182578 7/1998
JP 2002-30048 1/2002

OTHER PUBLICATIONS

Database CAPLUS on STN, Acc. No. 1977:452888, Pirkle et al., Journal of Organic Chemistry (1977), 42(14), p. 2436-2439 (abstract).*
International Search Report dated Aug. 24, 2004 based on International Application No. PCT/JP2004/007955, filed Jun. 8, 2004.
Török, Bèla et al., "Synthesis of Chiral Trifluoromethylated Amines by Palladium-Catalyzed Diastereoselective Hydrogenation-Hydrogenolysis Approach", Adv. Synth. Catal. 2003, 345, No. 1&2, pp. 165-168; XP-002989156.
Pirkle, W.H. et al., "Design of Chiral Derivatizing Agents for the Chromatographic Resolution of Optical Isomers. Asymmetric Synthesis of Some Chiral Fluoroalkylated Amines", J. Org. Chem., vol. 42, No. 14, 1977, pp. 2436-2439; XP-002989157.
Soloshonok Vadim et al., "Highly Enantioselective Transfer of Chirality from a Less to a More Configurationally Unstable Stereogenic Center. A Practical Asymmetric Synthesis of (Fluoroalkyl) amines via Biomimetic Transamination", J. Org. Chem. 1997, 62, pp. 3030-3031; XP-002291600.
European Search Reprot dated Nov. 27, 2007 (three (3) pages).

* cited by examiner

*Primary Examiner*—Brian J Davis
(74) *Attorney, Agent, or Firm*—Crowell & Moring LLP

(57) ABSTRACT

The present invention relates to a process for producing an optically active 1-alkyl-substituted 2,2,2-trifluoroethylamine, which is an important intermediate of medicines and agricultural chemicals, and which is represented by the formula [3] [in the formula R represents a lower alkyl group of a carbon and * represents an asymmetric carbon], or its salt by subjecting an optically active imine represented by the formula [1] to an asymmetric reduction under hydrogen atmosphere using a metal catalyst of Group VIII to convert it into an optically active secondary amine represented by the formula [2] and then by subjecting the secondary amine or its salt to hydrogenolysis.

[Chem. 23]

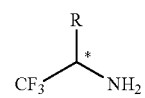

[3]

12 Claims, No Drawings

PROCESS FOR PRODUCING OPTICALLY ACTIVE 1-ALKYL-SUBSTITUTED 2,2,2-TRIFLUOROETHYLAMINE

TECHNICAL FIELD

The present invention relates to a process for producing optically active 1-alkyl-substituted 2,2,2-trifluoroethylamine, which is an important intermediate of medicines and agricultural chemicals.

BACKGROUND OF THE INVENTION

Optically active 1-alkyl-substituted 2,2,2-trifluoroethylamine, which is the target of the present invention, is an important intermediate of medicines and agricultural chemicals.

As processes for producing optically active 1-alkyl-substituted 2,2,2-trifluoroethylamine, there are reports of (1) a process (Patent Publication 1 and Non-patent Publication 1) in which (S)—N-(1-alkyl-2,2,2-trifluoroethylidene)-1-phenylethylamine is subjected to a [1,3]-proton shift reaction in the presence of a base, followed by hydrolysis; (2) a process (Patent Publication 2) in which a racemic mixture of 1-methyl-2,2,2-trifluoroethylamine is subjected to optical resolution with D-tartaric acid; (3) a process (Patent Publication 3) in which a carboxylic acid of L-alanine is fluorinated by $SF_4$; and (4) a process (Non-patent Publication 2) in which (R)-sulfinylimine is subjected to an asymmetric trifluoromethylation by trimethyl(trifluoromethyl)silane ($TMSCF_3$), followed by hydrolysis.

Patent Publication 1: Japanese Patent 3005669
Patent Publication 2: United States Patent specification 6204269
Patent Publication 3: European Patent Laid-open specification 0323637
Non-patent Publication 1: J. Org. Chem., (US), 1997, Vol. 62, No. 10, p. 3030-3031
Non-patent Publication 2: Angewandte Chemie, International Edition, (Germany), 2001, Vol. 40, No. 3, p 589-590

In the processes of Patent Publication 1 and Patent Publication 2, it was necessary to use 1 mol or more of expensive DBU (1,8-diazabicyclo[5,4,0]undec-7-ene) relative to 1 mol of the reaction substrate in order to obtain high chirality induction, and a purification by silica gel column chromatography was necessary to remove it.

In the process of Patent Publication 2, non-natural type tartaric acid as a resolving agent was expensive, and it was difficult to recover and reuse the same due to its water solubility. The theoretical yield was not greater than 50% due to optical resolution, and a complicated operation was necessary for racemization of an unnecessary isomer. In the process of Patent Publication 3, it was necessary to use dangerous $SF_4$, and the yield was not so high. In the process of Non-patent Publication 2, it was necessary to use optically active sulfinylimine that is difficult in industrial availability, and trimethyl(trifluoromethyl)silane ($TMSCF_3$) was a very expensive reagent.

Thus, there was a strong demand for a process that is capable of industrially producing optically active 1-alkyl-substituted 2,2,2-trifluoroethylamine.

SUMMARY OF THE INVENTION

There has been no report of a process, in which an optically active imine is subjected to an asymmetric reduction under hydrogen atmosphere using a metal catalyst of Group VIII (groups 8-10) to convert it to an optically active secondary amine, and in which the secondary amine or its salt is subjected to hydrogenolysis to produce optically active 1-alkyl-substituted 2,2,2-trifluoroethylamine or its salt, which is the target of the present invention.

It is an object of the present invention to provide a process for industrially producing optically active 1-alkyl-substituted 2,2,2-trifluoroethylamine, which is an important intermediate of medicines and agricultural chemicals.

According to the present invention, there is provided a process for producing an optically active 1-alkyl-substituted 2,2,2-trifluoroethylamine represented by the formula [3],

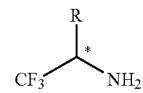

[3]

[in the formula R represents a lower alkyl group of a carbon number of 1 to 6 and * represents an asymmetric carbon] or its salt by subjecting an optically active imine represented by the formula [1],

[Chem. 1]

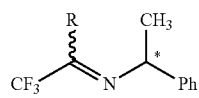

[1]

[in the formula R represents a lower alkyl group of a carbon number of 1 to 6, Ph represents a phenyl group, a wave line represents E configuration or Z configuration, and * represents an asymmetric carbon] to an asymmetric reduction under hydrogen atmosphere using a metal catalyst of Group VIII to convert it into an optically active secondary amine represented by the formula [2],

[Chem. 2]

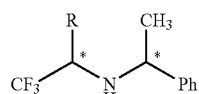

[2]

[in the formula R represents a lower alkyl group of a carbon number of 1 to 6, Ph represents a phenyl group, and * represents an asymmetric carbon] and then by subjecting the secondary amine or its salt to hydrogenolysis.

Furthermore, according to the present invention, the optically active imine represented by the formula [1] may be an optically active imine obtained by subjecting a trifluoromethyl alkyl ketone represented by the formula [4]

[Chem. 4]

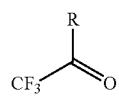

[4]

[in the formula R represents a lower alkyl group of a carbon number of 1 to 6] and an optically active 1-phenylethylamine represented by the formula [5],

[Chem. 5]

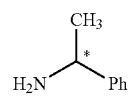

[5]

[in the formula Ph represents a phenyl group, and * represents an asymmetric carbon] to dehydration and condensation in the presence of an acid catalyst.

DETAILED DESCRIPTION

As a technique related to the present invention, there is a report of a process in which (S)—N-(1-phenyl-2,2,2-trifluoroethylidene)-1-phenylethylamine is subjected to an asymmetric reduction under hydrogen atmosphere using Pd catalyst to convert it into a corresponding optically active secondary amine (J. Org. Chem., (US), 1977, Vol. 42, No. 14, p. 2436-2439). However, it has almost not examined the extent of the substrate, to which this process can be applied, and detailed reaction conditions. There was no disclosure of an asymmetric reduction, which is the target of the present invention, using optically active N-(1-alkyl-substituted 2,2,2-trifluoroethylidene)-1-phenylethylamine as a reaction substrate.

The present inventors have found a phenomenon in which, in the case of using optically active N-(1-alkyl-substituted 2,2,2-trifluoroethylidene)-1-phenylethylamine as a reaction substrate, diastereo-face-selectivity of the asymmetric reduction is greatly affected by the temperature condition, and the diastereo-face-selectivity is reversed depending on the reaction temperature used. We have clarified that, particularly under low temperature, an optically active secondary amine having a relative configuration of R—R or S—S (the absolute configuration shown before the hyphen represents an absolute configuration on the side of 1-alkyl-substituted 2,2,2-trifluoroethyl group, and the absolute configuration shown after the hyphen represents an absolute configuration on the side of 1-phenylethyl group derived from the chiral aid group), which is advantageous in recrystallization purification of the after-mentioned salt, is obtained with a high diastereo-face-selectivity (see Table 1). We also found that the target optically active 1-alkyl-substituted 2,2,2-trifluoroethylamine or its salt can be obtained with high chemical purity and good yield by subjecting the obtained optically active secondary amine or its salt to hydrogenolysis, without lowering optical purity.

addition: In run 5, 5% Pd/C was further added by 2 wt %, and the reaction was continued for 16 hr. In run 8, 5% Pd/C was further added by 3 wt %, and the reaction was continued for 21 hr.

Furthermore, we have found that a purification with high diastereomeric excess (d. e.) can be achieved by converting the optically active secondary amine obtained by the asymmetric reduction into its salt, followed by recrystallization purification.

Therefore, it is possible to obtain the target optically active 1-alkyl-substituted 2,2,2-trifluoroethylamine with high optical purity by combining the above newly found production process and the purification process.

Furthermore, we have found an optically active secondary amine and its salt, which are novel compounds as useful intermediates, in the process for producing optically active 1-alkyl-substituted 2,2,2-trifluoroethylamine.

As mentioned above, the present inventors have found a novel process for producing optically active 1-alkyl-substituted 2,2,2-trifluoroethylamine and thus have completed the present invention.

The present production process is a very effective process for industrially producing optically active 1-alkyl-substituted 2,2,2-trifluoroethylamine, which is an important intermediate of medicines and agricultural chemicals, since each reaction step is high in selectivity and does almost not produce impurities that are difficult in separation.

A process for producing optically active 1-alkyl-substituted 2,2,2-trifluoroethylamine of the present invention is described in detail. The production steps of the present invention can be composed of four steps of (1) dehydration and condensation, (2) asymmetric reduction, (3) salt purification, and (4) hydrogenolysis (see scheme 1).

TABLE 1

| run | sub. | Pd/C | solvent | temp. | time | conv. | d.r. (S-S:R-S) | o.r. |
|---|---|---|---|---|---|---|---|---|
| 1 | 1.08 g (5.02 mmol) | 5% Pd/C (2 wt. %) | THF (1 M) | 60° C. | 8 h | 73% | 43:57 | 8.3% |
| 2 | 1.08 g (5.02 mmol) | 5% Pd/C (2 wt. %) | MeOH (1 M) | 60° C. | 8 h | 92% | 48:52 | 2.2% |
| 3 | 1.08 g (5.02 mmol) | 5% Pd/C (2 wt. %) | THF (1 M) | 30° C. | 8 h | 24% | 49:51 | 1.7% |
| 4 | 1.08 g (5.02 mmol) | 5% Pd/C (2 wt. %) | MeOH (1 M) | 30° C. | 8 h | 47% | 60:40 | 0.9% |
| 5 | 6.00 g (27.88 mmol) | 5% Pd/C (2 wt. %) addition 5% Pd/C (2 wt. %) | MeOH (1 M) | 20° C. | 3 days + 16 h | 80% 93% | 66:34 68:32 | 0.8% 1.1% |
| 6 | 2.00 g (9.29 mmol) | 5% Pd/C (5 wt. %) | MeOH (1 M) | 20° C. | 24 h | 93% | 60:40 | 1.2% |
| 7 | 53.80 g (249.99 mmol) | 5% Pd/C (5 wt. %) | MeOH (1 M) | 20° C. | 24 h | 96% | 60:40 | 0.9% |
| 8 | 2.00 g (9.29 mmol) | 5% Pd/C (2 wt. %) addition 5% Pd/C (3 wt. %) | MeOH (1 M) | 0° C. | 18 h + 21 h | 20% 61% | 79:21 77:23 | 0.0% 0.0% |
| 9 | 4.30 g (19.98 mmol) | 5% Pd/C (5 wt. %) | MeOH (1 M) | 0° C. | 3 days | 95% | 75:25 | 0.2% |

Explanation of the abbreviations of Table 1 is as follows.
sub.: optically active imine.
temp.: reaction temperature.
conv.: conversion.
d.r.: diastereomer ratio.
o.r.: composition ratio of excessive reaction product 1-methyl-2,2,2-trifluoroethylamine.
wt.: weight
5% Pd/C: one prepared by mixing "a palladium-carbon powder", in which Pd of 5 g (in terms of metallic atom) is carried per 100 g of activated carbon, with water of the same weight as this and by adjusting wetness.
1 M: 1 mmol/ml.
addition: In run 5, 5% Pd/C was futher added by 2 wt. %, and the reaction was continued for 16 hr. In run 8, 5% Pd/C was further added by 3 wt. %, and the reaction was continued for 21 hr.

[Chem. 6]

Scheme 1

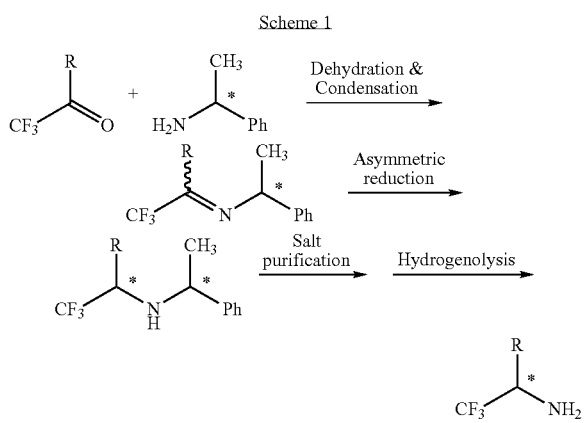

At first, the dehydration and condensation of the first step are described in detail. The dehydration and condensation of the first step are conducted by subjecting a trifluoromethyl alkyl ketone represented by the formula [4] and an optically active 1-phenylethylamine represented by the formula [5] to dehydration and condensation in the presence of an acid catalyst. Examples of conducting dehydration and condensation using no catalyst are shown in the above Patent Publication 1 and Non-patent Publication 1. Although it is not the dehydration and condensation of a trifluoromethyl alkyl ketone, which is the target of the present invention, there is also shown an example of conducting the reaction using paratoluene sulfonic acid (PTS) as an acid catalyst in analogous dehydration and condensation (J. Org. Chem., (US), 1977, Vol. 42, No. 14, p. 2436-2439).

As R of a trifluoromethyl alkyl ketone represented by the formula [4], there are cited methyl, ethyl, 1-propyl, 2-propyl, cyclopropyl, 1-butyl, 2-butyl, 2-methyl-1-propyl, tert-butyl, cyclobutyl, 1-pentyl, 2-pentyl, 3-pentyl, neopentyl, tert-amyl, cyclopentyl, 1-hexyl, 2-hexyl, 3-hexyl, cyclohexyl and the like. Although trifluoromethyl alkyl ketones shown herein include novel compounds, it is possible to similarly produce them by using organic metal reagents having different alkyl groups, with reference to J. Org. Chem., (US), 1987, Vol. 52, No. 22, p. 5027-5030.

As to the amount of a trifluoromethyl alkyl ketone represented by the formula [4] to be used, it suffices to use 1 mol or greater, generally preferably 1-10 mols, particularly more preferably 1-5 mols, relative to 1 mol of an optically active 1-phenylethylamine represented by the formula [5].

As the absolute configuration of the asymmetric carbon of an optically active 1-phenylethylamine represented by the formula [5], both of R configuration and S configuration are possible. It is possible to suitably use them depending on the absolute configuration of the target optically active 1-alkyl-substituted 2,2,2-trifluoroethylamine.

As to optical purity of an optically active 1-phenylethylamine represented by the formula [5], it suffices to use one having an enantiomeric excess (e. e.) of 95% or greater, generally preferably 97% e. e. or greater, particularly preferably 99% e. e. or greater.

As the acid catalyst, there are cited organic acids such as formic acid, acetic acid, propionic acid, trifluoroacetic acid, methanesulfonic acid, trifluoromethanesulfonic acid, benzenesulfonic acid, paratoluenesulfonic acid (PTS), pyridiniumparatoluene sulfonate (PPTS) and 10-camphorsulfonic acid; ion exchange resins such as Amberlyst H-15 and Dowex 50W-X8; and inorganic acids such as hydrochloric acid, hydrobromic acid, sulfuric acid, phosphoric acid, zinc chloride, and titanium tetrachloride. Of these, pyridiniumparatoluene sulfonate (PPTS) is particularly more preferable. With no catalyst used in the above Patent Publication 1 and Non-patent Publication 1, the reaction rate is slow. With paratoluenesulfonic acid (PTS) used in J. Org. Chem., (US), 1977, Vol. 42, acid strength becomes excessive, and yield is lowered.

The amount of the acid catalyst used may be in catalytic amount, generally preferably 0.001-0.5 mols, particularly more preferably 0.01-0.25 mols, relative to 1 mol of optically active 1-phenylethylamine represented by the formula [5].

The present reaction is dehydration and condensation of trifluoromethyl alkyl ketone and optically active 1-phenylethylamine. Therefore, it is preferable to conduct the reaction while removing water produced as a by-product under acidic condition. For example, water as a by-product is removed by using a reaction solvent that is immiscible with water, that is lower than water in specific gravity and that forms an azeotrope with water and by using a Dean-Stark tube under reflux condition, or water as a by-product is removed by a desiccant such as synthetic zeolite (trade name: Molecular Sieve), anhydrous phosphoric acid, anhydrous magnesium sulfate, and anhydrous sodium sulfate. In dehydration and condensation of trifluoromethyl alkyl ketone and optically active 1-phenylethylamine, which is the target of the present invention, it is possible to obtain a sufficient reaction rate, even if the above water removal operation is not conducted.

As the reaction solvent, an aromatic hydrocarbon such as benzene, toluene, ethylbenzene, xylene or mesitylene is preferable. In particular, toluene is more preferable. It is possible to use these reaction solvents alone or in combination.

The amount of the reaction solvent used may be 0.01 L (liter) or greater, generally preferably 0.05-20 L, particularly more preferably 0.1-10 L, relative to 1 mole of optically active 1-phenylethylamine represented by the formula [5].

The temperature condition is 0-200° C., generally preferably 3-175° C., particularly more preferably 5-150° C. In the case of conducting the reaction under a temperature condition that is higher than boiling point of the trifluoromethyl alkyl ketone used, it is also possible to use a pressure-proof reaction vessel.

Although the reaction time is 0.1-72 hr, it varies depending on the reaction substrate and the reaction condition. Therefore, it is preferable to trace the progress of the reaction by an analytical means such as gas chromatography, liquid chromatography or NMR and to regard the time, at which the raw material has almost disappeared, as end point.

The post-treatment is not particularly limited. It is possible to obtain a crude product by conducting a normal post-treatment operation after the termination of the reaction. In particular, it is possible to selectively remove the unreacted optically active 1-phenylethylamine by washing the reaction-terminated liquid or an organic layer containing the target optically active imine represented by the formula [1] with ammonium chloride aqueous solution. It is possible to obtain the target optically active imine represented by the formula [1], according to need, by subjecting the crude product to a purification operation such as activated carbon treatment, distillation and recrystallization. It is possible to use the reaction-terminated liquid in the asymmetric reduction of the second step without conducting any post-treatment operation.

With respect to geometrical isomerism at the double bond of the target optically active imine represented by the formula

[1], there exists E configuration or Z configuration. Its formation ratio varies depending on the reaction substrate and the reaction condition.

Next, the asymmetric reduction of the second step is described in detail. The asymmetric reduction of the second step is conducted by subjecting the optically active imine represented by the formula [1] to an asymmetric reduction under hydrogen atmosphere using a metal catalyst of the group VIII.

There exists an R configuration or S configuration as the absolute configuration of an asymmetric carbon, which has been newly formed by a chirality induction, of the target optically active secondary amine represented by the formula [2]. Its formation ratio varies depending on the reaction substrate and the reaction condition. As a combination of the absolute configurations by the two asymmetric carbons, there exists R—R configuration, S—R configuration, R—S configuration or S—S configuration.

As the metal catalyst of the group VIII (the groups 8-10), there are cited platinum catalysts such as platinum oxide, platinum/active carbon and platinum black; nickel catalysts such as reduced nickel, Raney nickel and platinum-Raney nickel; cobalt catalysts such as Raney cobalt; ruthenium catalysts such as ruthenium oxide and ruthenium/active carbon; rhodium catalysts such as rhodium/active carbon, rhodium/alumina and rhodium-platinum oxide; iridium catalysts such as iridium black; and palladium catalysts such as palladium/active carbon, palladium hydroxide, palladium black, palladium/barium sulfate, palladium/strontium carbonate, palladium/calcium carbonate, palladium/calcium carbonate-lead diacetate, palladium/barium sulfate-quinoline, palladium/alumina, palladium sponge, palladium chloride, palladium acetate, palladium acetylacetonate, bis(dibenzylideneacetone)palladium, tetrakis(triphenylphosphine)palladium, dichloro[bis(triphenylphosphine)]palladium, dichloro[bis(diphenylphosphino)methane]palladium, dichloro[bis(diphenylphosphino)ethane]palladium, dichloro[1,3-bis(diphenylphosphino)propane]palladium, dichloro[1,4-bis(diphenylphosphino)butane]palladium, dichloro(1,5-cyclooctadiene)palladium, dichloro[bis(benzonitrile)]palladium, dichloro[bis(acetonitrile)]palladium, and [bis(triphenylphosphine)]palladium acetate. Among these, platinum catalysts, nickel catalysts, ruthenium catalysts, rhodium catalysts and palladium catalysts are preferable, and platinum/active carbon, Raney nickel, ruthenium/active carbon, rhodium/active carbon and palladium/active carbon are particularly more preferable. These metal catalysts of the group VIII can be used alone or in combination. In the case of using a catalyst in which a metal is loaded on a support, the loaded amount is 0.1-50 wt %, generally preferably 0.5-30 wt %, and particularly more preferably 1-20 wt %. In addition, in order to enhance safety during handling or to prevent oxidation of the metal surface, it is also possible to use one stored in water or mineral oil.

The amount of the metal catalyst of the group VIII used may be in catalytic amount, generally preferably 0.00001-0.1 g, particularly more preferably 0.00005-0.05 g, in terms of metal, relative to 1 g of the optically active imine represented by the formula [1].

The amount of hydrogen used may be 1 mol or greater relative to 1 mol of the optically active imine represented by the formula [1]. In general, the reaction is conducted under hydrogen atmosphere, and it is used in large excess.

The hydrogen pressure of hydrogen atmosphere is 5 MPa or lower, generally preferably 0.01-3 MPa, particularly more preferably 0.05-2 MPa.

As the reaction solvent, there are cited aliphatic hydrocarbons such as n-pentane, n-hexane, cyclohexane, and n-heptane; aromatic hydrocarbons such as benzene, toluene, ethylbenzene, xylene, and mesitylene; ethers such as diethyl ether, tetrahydrofuran, tert-butyl methyl ether, and 1,4-dioxane; esters such as ethyl acetate and n-butyl acetate; alcohols such as methanol, ethanol, n-propanol, i-propanol, n-butanol, n-pentanol, n-hexanol, cyclohexanol, n-heptanol, and n-octanol; carboxylic acids such as acetic acid, propionic acid, and butyric acid; acidic aqueous solutions such as hydrochloric acid, sulfuric acid, hydrobromic acid, paratoluenesulfonic acid, and 10-camphorsulfonic acid; and water. Of these, toluene, tetrahydrofuran, ethyl acetate, methanol, ethanol, n-propanol, i-propanol, n-butanol, n-pentanol, n-hexanol, cyclohexanol, n-heptanol, n-octanol, acetic acid, acidic aqueous solution of hydrochloric acid, and acidic aqueous solution of hydrobromic acid are preferable. In particular, methanol, ethanol, n-propanol, i-propanol, n-butanol, n-pentanol, n-hexanol, cyclohexanol, n-heptanol, n-octanol, acidic aqueous solution of hydrochloric acid, and acidic aqueous solution of hydrobromic acid are more preferable. These reaction solvents can be used alone or in combination.

The amount of the reaction solvent used may be 0.01 L (liter) or greater, generally preferably 0.05-20 L, particularly more preferably 0.1-10 L, relative to 1 mol of the optically active imine represented by the formula [1].

The temperature condition is generally −50 to +100° C., preferably −40 to +60° C., particularly more preferably −30 to +10° C.

This temperature condition is particularly important in the present reaction. Under a low temperature of 10° C. or lower, it is possible not only to obtain the optically active secondary amine having a relative configuration of R—R or S—S, which is advantageous in the salt purification of the third step, with high diastereo-face-selectivity, but also to almost completely control by-production of 1-alkyl-substituted 2,2,2-trifluoroethylamine of low optical purity due to an excessive reaction (see Table 1). On the other hand, we cannot say that the lower the reaction temperature is, the more preferable result we can obtain. Under an extremely low temperature condition of lower than −50° C., the reaction rate becomes very low. Thus, it is not necessarily a practical temperature condition. Under a temperature condition of higher than 100° C., it is not possible to obtain the optically active secondary amine having a relative configuration of R—R or S—S, which is advantageous in the salt purification of the third step, with high diastereo-face-selectivity. Furthermore, it is accompanied with by-production of 1-alkyl-substituted 2,2,2-trifluoroethylamine of low optical purity due to an excessive reaction. Therefore, it is not an effective temperature condition.

Although the reaction time is generally 0.1-240 hr, it varies depending on the reaction substrate and the reaction condition. Therefore, it is preferable to trace the progress of the reaction by an analytical means such as gas chromatography, liquid chromatography or NMR and to regard the time, at which the raw material has almost disappeared, as end point.

The post-treatment is not particularly limited. It is possible to obtain a crude product by conducting a normal post-treatment operation after the termination of the reaction. In case that the target optically active secondary amine represented by the formula [2] is low in boiling point or high in volatility, it can be recovered in the form of salt by conducting a post-treatment operation such as concentration, after previously adding an acid, which corresponds to the salt induced by the third step, to a filtrate obtained by removing the metal catalyst of the group VIII from the reaction-terminated liquid by Cellite filtration or the like. In contrast, in case that the target optically active secondary amine represented by the formula [2] is high in boiling point and also low in volatility and that the reaction has been conducted by using an acidic aqueous solution of an acid as the reaction solvent, it is possible to efficiently recover the target optically active secondary amine represented by the formula [2] as a free base by conducting a neutralization with a basic aqueous solution of an inorganic base and then by conducing an extraction with an organic solvent. It is possible to obtain the target optically active secondary amine represented by the formula [2] with high chemical purity, according to need, by subjecting the crude product to a purification operation such as activated carbon treatment, distillation and recrystallization.

Next, the salt purification of the third step is described in detail. The salt purification of the third step is conducted by converting the optically active secondary amine represented by the formula [2] into its salt, followed by recrystallization purification.

As the acid, inorganic acids and organic acids are cited.

As the inorganic acid, there are cited carbonic acid, hydrochloric acid, sulfuric acid, nitric acid, hydrobromic acid, hydroiodic acid, phosphoric acid, boric acid, perchloric acid, and the like. Of these, hydrochloric acid and hydrobromic acid are preferable. In particular, hydrobromic acid is more preferable.

As the organic acid, there are cited aliphatic carboxylic acids such as acetic acid, propionic acid, butyric acid, isobutyric acid, valeric acid, isovaleric acid, hexanoic acid, heptanoic acid, cyclohexanecarboxylic acid, octanoic acid, phenylacetic acid and 3-phenylpropionic acid; haloalkylcarboxylic acids such as chloroacetic acid, dichloroacetic acid, trichloroacetic acid, fluoroacetic acid, difluoroacetic acid, trifluoroacetic acid, bromoacetic acid, iodoacetic acid, 2-chloropropionic acid and 3-chloropropionic acid; unsaturated carboxylic acids such as acrylic acid, crotonic acid, citraconic acid, maleic acid, fumaric acid and cis- or trans-cinnamic acid; aromatic carboxylic acids such as benzoic acid, o-, m- or p-toluic acid, o-, m- or p-fluorobenzoic acid, o-, m- or p-chlorobenzoic acid, o-, m- or p-bromobenzoic acid, o-, m- or p-iodobenzoic acid, o, m- or p-hydroxybenzoic acid, o-, m- or p-anisic acid, o-, m- or p-aminobenzoic acid, o-, m- or p-nitrobenzoic acid, o-, m- or p-cyanobenzoic acid, m- or p-benzenedicarboxylic acid (phthalic acid, isophthalic acid or terephthalic acid), α-, β- or γ-picolinic acid, 2,6-pyridinedicarboxylic acid and 1- or 2-naphthoic acid; sulfonic acids such as methanesulfonic acid, chloromethanesulfonic acid, trifluoromethanesulfonic acid, benzenesulfonic acid, p-toluenesulfonic acid and p-phenolsulfonic acid; optically active carboxylic acids such as lactic acid, malic acid, tartaric acid, dibenzoyltartaric acid, 2-phenylpropionic acid, mandelic acid, camphoric acid and cis-2-benzamidocyclohexanecarboxylic acid; optically active sulfonic acids such as phenylethanesulfonic acid and 10-camphorsulfonic acid; optically active phosphoric acids such as 2,2=-(1,1=-binaphthyl)phosphoric acid; optically active amino acids such as 4-aminobutyric acid, phenylglycine and aspartic acid; optically active N-acylamino acids such as pyroglutamic acid, N-acetyl-3,5-dibromo-tyrosine, N-acyl-phenylalanine, N-acyl-aspartic acid, N-acylglutamic acid and N-acylproline (wherein, N-acyl group represents acetyl group, benzyloxycarbonyl group, benzoyl group, benzenesulfonyl group, p-toluenesulfonyl group and the like), and other organic acids such as formic acid, oxalic acid, malonic acid, succinic acid, adipic acid, pimelic acid, cyanoacetic acid, citric acid, glycolic acid, glyoxylic acid, pyruvic acid, levulinic acid, oxaloacetic acid, mercaptoacetic acid, phenoxyacetic acid and picric acid. The optically active carboxylic acids, the optically active sulfonic acids, the optically active phosphoric acids, the optically active amino acids and the optically active N-acylamino acids have optical isomers, and their both optical isomers can be used. Of these, optically active 10-camphorsulfonic acid is particularly more preferable.

The amount of the acid used may be 0.3 moles or greater, generally preferably 0.4-5 moles, particularly more preferably 0.5-3 moles, relative to 1 mol of the optically active secondary amine represented by the formula [2].

The process for preparing the salt may be suitably selected depending on a combination of the optically active secondary amine represented by the formula [2] and the acid. Usually, it can be prepared by directly adding the optically active secondary amine represented by the formula [2] and the acid to the recrystallization solvent and then mixing, or by previously preparing the respective solutions and then mixing the solutions together. The precipitation of the crystals can be conducted directly from the prepared salt solution. Alternatively, it can be conducted by once concentrating the prepared salt solution, followed by dissolution again in the recrystallization solvent.

The recrystallization solvent is not particularly limited, as long as it does not react with the optically active secondary amine represented by the formula [2], the acid or the salt prepared from these. It can suitably be selected depending on the diastereomer excess (d. e.) prior to the purification, or the target diastereomer excess (d. e.) after the purification and the recovery and the like.

As the recrystallization solvent, there are cited aliphatic hydrocarbons such as n-pentane, n-hexane, cyclohexane, and n-heptane; aromatic hydrocarbons such as benzene, toluene, ethylbenzene, xylene, and mesitylene; halogenated hydrocarbons such as methylene chloride, chloroform, and 1,2-dichloroethane; ethers such as diethyl ether, tetrahydrofuran, t-butyl methyl ether, and 1,4-dioxane; ketones such as acetone, methyl ethyl ketone, and methyl isobutyl ketone; esters such as ethyl acetate and n-butyl acetate; nitriles such as acetonitrile and propionitrile; alcohols such as methanol, ethanol, n-propanol, i-propanol, and n-butanol; and water. Of these, preferable ones are n-hexane, n-heptane, toluene, methylene chloride, tetrahydrofuran, t-butyl methyl ether, acetone, methyl ethyl ketone, ethyl acetate, acetonitrile, methanol, ethanol, n-propanol, i-propanol, and n-butanol. In particular, n-hexane, n-heptane, toluene, methanol, ethanol, n-propanol, i-propanol and n-butanol are more preferable. These recrystallization solvents can be used alone or in combination.

The amount of the recrystallization solvent used is not particularly limited, to the extent that the salt prior to the purification is completely or partially dissolved upon heating. It may be suitably selected depending on the diastereomer excess (d. e.) prior to the purification, or the target diastereomer excess (d. e.) after the purification and the recovery and the like. It may be used in 0.01 L (liter) or greater, generally preferably 0.03-20 L, particularly more preferably 0.05-10 L, relative to 1 mol of the salt prior to the purification of the optically active secondary amine represented by the formula [2].

Although the relative configuration of two asymmetric carbons of the optically active secondary amine represented by the formula [2], which is subjected to the salt purification, is not particularly limited, R—R configuration or S—S configuration can more advantageously be purified, as compared with S—R configuration or R—S configuration.

The optically active secondary amine represented by the formula [2], which is subjected to the salt purification, is not particularly limited in diastereomer excess (d. e.). It is usually preferably 5% d. e. or greater, particularly more preferably 10% d. e. or greater.

In the salt purification, it is possible to efficiently precipitate the crystals by adding seed crystals. Diastereomer excess (d. e.) of seed crystals used may be 95% d. e. or greater, generally preferably 97% d. e. or greater, particularly more preferably 99% d. e. or greater.

The amount of seed crystals used may be 0.0001 g or greater, generally preferably 0.001-20 g, particularly more preferably 0.01-10 g.

The temperature condition can suitably be selected depending on boiling point and freezing point of the recrystallization solvent used. In general, it is preferable that the salt prior to purification is dissolved at a temperature of from room temperature (25° C.) to a temperature close to boiling point of the recrystallization solvent and then the crystals are sufficiently precipitated at −20 to +20° C. In general, it is preferable to add seed crystals during the temperature decrease.

In the present purification, the precipitated crystals are generally improved in diastereomer excess (d. e.). Therefore, it is possible to obtain a salt of high diastereomer excess (d. e.) by recovering the precipitated crystals by filtration or the like. In some cases, the mother liquor is improved in diastereomer excess (d. e.) depending on the combination of the optically active secondary amine represented by the formula [2] and the acid. Thus, it is possible to obtain a solution containing a salt of high diastereomer excess (d. e.) by removing the precipitated crystals by filtration or the like. It can be purified to have a higher diastereomer excess (d. e.) by further repeating these purification operations.

In the hydrogenolysis of the fourth step, the obtained salt as it is or the free base restored by neutralization can be used. As a method for making it return to the free base, it is possible to efficiently recover the free base by neutralizing it with a basic aqueous solution of an inorganic base, followed by extraction with organic solvent.

Finally, the hydrogenolysis of the fourth step is explained in detail. The hydrogenolysis of the fourth step is conducted by subjecting the optically active secondary amine represented by the formula [2] or its salt to hydrogenolysis.

In the present hydrogenolysis, it is possible to obtain the optically active 1-alkyl-substituted 2,2,2-trifluoroethylamine or R configuration of its salt, without lowering optical purity, from the optically active secondary amine represented by the formula [2] or R—R configuration or R—S configuration of its salt. On the other hand, it is possible to obtain S configuration, without lowering optical purity, from S—R configuration or S—S configuration.

The present hydrogenolysis can be conducted by using a metal catalyst of the group VIII under hydrogen atmosphere. Therefore, it is possible to similarly use the reaction condition used in the asymmetric reduction of the second step, as the present reaction condition. In this case, it is conducted by respectively replacing the optically active imine represented by the formula [1] and the optically active secondary amine represented by the formula [2] with the optically active secondary amine represented by the formula [2] and the optically active 1-alkyl-substituted 2,2,2-trifluoroethylamine represented by the formula [3]. Therefore, there are omitted similar descriptions (for example, the metal catalyst of the group VIII, the amount of the metal catalyst of the group VIII used, the amount of hydrogen used, the hydrogen pressure, the reaction solvent, the amount of the reaction solvent used, the reaction time, and the post-treatment). The hydrogenolysis of the fourth step and the asymmetric reduction of the second step are vastly different from each other in temperature condition as an important reaction condition. It is described in detail in the following.

It is more efficient and practical to conduct the hydrogenolysis under a temperature condition that is higher than that of the asymmetric reduction. The temperature condition is 20-200° C., generally preferably 30-150° C., particularly more preferably 40-100° C.

The post-treatment is described in detail. The post-treatment is not particularly limited. It is possible to obtain a crude product by conducting a normal post-treatment operation after the termination of the reaction. In case that the target optically active 1-alkyl-substituted 2,2,2-trifluoroethylamine represented by the formula [3] is low in boiling point or high in volatility, it can be recovered in the form of salt by conducting a post-treatment operation such as concentration, after previously adding an acid, which has been described in the salt purification of the third step, to a filtrate obtained by removing the metal catalyst of the group VIII from the reaction-terminated liquid by Cellite filtration or the like. In contrast, in case that the target optically active 1-alkyl-substituted 2,2,2-trifluoroethylamine represented by the formula [3] is high in boiling point and also low in volatility and that the reaction has been conducted by using a salt of the optically active secondary amine represented by the formula [2], or the reaction has been conducted by using an acidic aqueous solution of an acid as the reaction solvent, it is possible to efficiently recover the target optically active 1-alkyl-substituted 2,2,2-trifluoroethylamine represented by the formula [3] as a free base by conducting a neutralization with a basic aqueous solution of an inorganic base and then by conducing an extraction with an organic solvent. It is possible to obtain the target optically active 1-alkyl-substituted 2,2,2-trifluoroethylamine represented by the formula [3] with high chemical purity, according to need, by subjecting the crude product to a purification operation such as activated carbon treatment, distillation and recrystallization.

In the following, embodiments of the present invention are specifically described by examples. The present invention is, however, not limited to these examples.

EXAMPLE 1

Dehydration and Condensation 1

A toluene solution (the amount of toluene used: 300 ml) of (S)-1-phenylethylamine of 132.00 g (1.089 mol, 1.00 eq) was added under cooling with ice to a toluene solution (the amount of toluene used: 700 ml) of 1,1,1-trifluoroacetone of 239.23 g (2.135 mol, 1.96 eq), following by stirring at an internal temperature of 10-22° C. for 2 hr and 40 min. Furthermore, 13.69 g (0.054 mol, 0.05 eq) of PPTS were added. Stirring was conducted at an internal temperature of 82-113° C. for 18 hr and 5 min, and water produced as a by-product was removed by a Dean-Stark tube. Conversion of the reaction was determined by gas chromatography to be 88.1%. The reaction-terminated liquid was washed four times with 250 ml of a saturated ammonium chloride aqueous solution. The recovered organic layer was concentrated under reduced pressure, followed by vacuum drying, thereby obtaining 239.67 g of a crude product of an optically active imine represented by the following formula.

[Chem. 7]

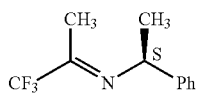

Recovery of the organic matter of the crude product was quantitative. Gas chromatography purity of the crude product was 90.6%. The total amount of the crude product was subjected to distillation purification, thereby obtaining 167.11 g of the distillation purification product (80-84° C./1600 Pa-2130 Pa). Gas chromatography purity of the distillation purification product was 94.6%. The total yield of the dehydration and condensation and the distillation purification was 67%. $^1$H-NMR spectrum and $^{19}$F-NMR spectrum are shown in the following. Stereochemistry of the double bond was determined to be E configuration by $^1$H-NMR spectrum and $^{19}$F-NMR spectrum.

1H-NMR (standard substance: TMS, solvent: CDCl$_3$), δ ppm: 1.50(d, 6.8 Hz, 3H), 2.03(s, 3H), 4.71(q, 6.8 Hz, 1H), 7.20-7.40(Ar—H, 5H).

$^{19}$F-NMR (standard substance: C$_6$F$_6$, solvent: CDCl$_3$), δ ppm: 87.01(s, 3 F).

EXAMPLE 2

Asymmetric Reduction 1

Run 9 of Table 1 is shown in the following as a representative example. Runs 1-8 were conducted under reaction conditions shown in Table 1 in a way similar to Run 9.

To 20 ml of methanol, there were added 4.30 g (19.98 mmol) of the distillation purification product of the optically active imine produced by Example 1 and 0.22 g (5 wt % relative to the optically active imine) of 5% Pd/C (50 wt % wet) (referred to one prepared by mixing "palladium-carbon powder", in which 5 g of Pd (in terms of metallic atom) have been loaded per 100 g of activated carbon, with water in the same weight as this, followed by wetness adjustment, hereinafter the same). The internal temperature was lowered to 0° C., the hydrogen pressure was set to 0.5 MPa, and stirring was conducted at 0° C. for 3 days. The reaction-terminated liquid was subjected to Cellite filtration. Conversion and diastereomer ratio were determined by $^1$H-NMR spectrum, and compositional ratio of an excessive reaction product 1-methyl-2,2,2-trifluoroethylamine was determined by gas chromatography. They were respectively 95%, S—S:R—S=75:25, and 0.2%. A portion of the filtrate obtained by Cellite filtration was concentrated under reduced pressure, followed by vacuum drying. The production of an optically active secondary amine represented by the following formula was confirmed by $^1$H-NMR spectrum and $^{19}$F-NMR spectrum.

[Chem. 8]

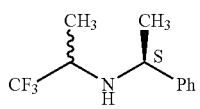

$^1$H-NMR spectrum and $^{19}$F-NMR spectrum are shown in the following.

$^1$H-NMR (standard substance: TMS, solvent: CDCl$_3$)

S—S configuration (major)/δ ppm: 1.11(d, 6.6 Hz, 3H), 1.32(d, 6.6 Hz, 3H), 2.94(septet, 6.6 Hz, 1 H), 4.05(q, 6.6 Hz, 1H), 7.20-7.43(Ar—H, 5H), and it was not possible to assign a broad peat derived from —NH.

R—S configuration (minor)/δ ppm: 1.22(d,6.6 Hz,3H), 1.36(d,6.6 Hz,3H), 2.99(septet,6.6 Hz,1H), 3.97(q,6.6 Hz,1H), 7.20-7.43(Ar—H,5H), and it was not possible to assign a broad peat derived from —NH.

$^{19}$F-NMR (standard substance: C$_6$F$_6$, solvent: CDCl$_3$)

S—S configuration (major)/δ ppm: 85.58(d,6.6 Hz,3F).

R—S configuration (minor)/δ ppm: 84.33(d, 6.6 Hz,3F).

EXAMPLE 3

Dehydration and Condensation 2

A toluene solution (the amount of toluene used: 1000 ml) of (S)-1-phenylethylamine of 734.38 g (6.060 mol, 1.00 eq) was added under cooling with ice to a toluene solution (the amount of toluene used: 4600 ml) of 1,1,1-trifluoroacetone of 1158.56 g (10.340 mol, 1.71 eq), followed by stirring at an internal temperature of 32-34° C. for 2 hr. Furthermore, there was added a PPTS toluene solution prepared by adding 57.64 g (0.303 mol, 0.05 eq) of PTS monohydrate and 24.00 g (0.303 mol, 0.05 eq) of pyridine to 460 ml of toluene and then by stirring, followed by stirring at an internal temperature of 60-84° C. for 7 hr and 30 min. Conversion of the reaction was determined by gas chromatography to be not lower than 85%. The reaction-terminated liquid was washed one time with 1000 ml of 1N sodium hydroxide aqueous solution, four times with 1500 ml of 3N ammonium chloride aqueous solution, and then one time with 1000 ml of 10% brine. The recovered organic layer was concentrated under reduced pressure, followed by vacuum drying, thereby obtaining a crude product of an optically active imine represented by the following formula.

[Chem. 9]

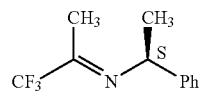

Gas chromatography purity of the crude product was 82.7%.

Furthermore, the production was conducted similarly by using 1148.18 g (10.247 mol, 1.70 eq) of 1,1,1-trifluoroacetone, 730.43 g (6.028 mol) of (S)-1-phenylethylamine, 57.33 g (0.301 mol, 0.05 eq) of PTS monohydrate, 23.73 g (0.300 mol, 0.05 eq) of pyridine, and 6000 ml of toluene (the total amount in use).

These crude products were combined together in the total amount and subjected to a distillation purification, thereby obtaining b 2213.03 g of a distillation purification product (79-85° C./1200 Pa-1330 Pa). Gas chromatography purification of the distillation purification product was 85.6%. The total yield of the dehydration and condensation and the distillation purification was 73%. $^1$H-NMR spectrum and $^{19}$F-NMR spectrum were similar to those of Example 1. Stereochemistry of the double bond was determined to be E configuration by $^1$H-NMR spectrum and $^{19}$F-NMR spectrum.

EXAMPLE 4

Asymmetric Reduction 2

To 48.382 L of methanol, there were added 10.411 kg (41.023 mol; gas chromatography purity: 84.8%) of the distillation purification product of the optically active imine produced similar to Example 3 and 0.521 kg (5.9 wt % relative to the optically active imine) of 5% Pd/C (50 wt % wet). The internal temperature was lowered to 0° C., the hydrogen pressure was set to 0.50-0.52 MPa, and stirring was conducted at −1-0° C. for 53 hr and 40 min. The reaction-terminated liquid was subjected to Cellite filtration, and the residue was washed with 13.148 L of methanol. Conversion and diastereomer ratio were determined by $^1$H-NMR spectrum, and compositional ratio of an excessive reaction product 1-methyl-2,2,2-trifluoroethylamine was determined by gas chromatography. They were respectively 94%, S—S:R—S=70:30, and 0.1%. The filtrate (a portion (427.56 g) is used for Example 5) was concentrated under reduced pressure, thereby obtaining 11.196 kg of a crude product of an optically active secondary amine represented by the following formula.

[Chem. 10]

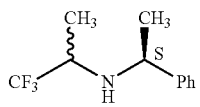

According to the internal standard method of $^{19}$F-NMR spectrum, the quantified value of the target substance in the crude product was 6.867 kg. The yield was 77%. $^1$H-NMR spectrum and $^{19}$F-NMR spectrum were similar to Example 2.

EXAMPLE 5

Salt Purification 1

427.56 g of the filtrate obtained by Cellite filtration of Example 4 were used. The content was quantified by the internal standard method of $^{19}$F-NMR spectrum. With this, the optically active secondary amine was in 54.33 g (250.10 mmol, 1.00 eq). To the total amount of the filtrate 46.35 g (274.97 mmol, 1.10 eq) of 48% hydrobromic acid were added under cooling with ice, followed by concentration under reduced pressure of methanol and water and then vacuum drying, thereby obtaining a salt of optically active secondary amine prior to purification, which is represented by the following formula.

[Chem. 11]

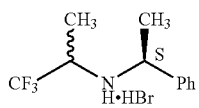

To the total amount of the salt of optically active secondary amine prior to purification 112 ml of i-propanol were added, followed by dissolution under reflux heating with stirring. With stirring, the temperature was gradually lowered. At 67° C., 0.10 g of the seed crystals were added, followed by cooling to room temperature (25° C.) by spending the entire night. Furthermore, stirring was conducted under cooling with ice for 1 hr. The precipitated crystals were filtered. The precipitated crystals were washed with a mixed liquid of 12 ml of i-propanol and 10 ml of n-hexane, followed by drying under reduced pressure and then vacuum drying, thereby obtaining 38.57 g of a salt (once recrystallized product) of the optically active secondary amine after purification, which is represented by the following formula.

[Chem. 12]

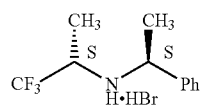

The once crystallized product was neutralized with 1N sodium hydroxide aqueous solution, followed by extraction with ethyl acetate. The diastereomer excess (d. e.) was determined by gas chromatography to be 94.9% d.e.

To the total amount of the once recrystallized product 193 ml of i-propanol were added, followed by dissolution under reflux heating with stirring. With stirring, the temperature was gradually lowered. At 65° C., 0.10 g of the seed crystals were added, followed by cooling to room temperature (25° C.) by spending the entire night. Furthermore, stirring was conducted under cooling with ice for 1 hr. The precipitated crystals were filtered. The precipitated crystals were washed with a mixed liquid of 10 ml of i-propanol and 10 ml of n-hexane, followed by drying under reduced pressure and then vacuum drying, thereby obtaining 33.55 g of a salt (twice recrystallized product) of the optically active secondary amine after purification, which is represented by the above formula. The total recovery of the recrystallization purification to S—S configuration was 64%. The twice recrystallized product was neutralized with 1N sodium hydroxide aqueous solution, followed by extraction with ethyl acetate. The chemical purity and the diastereomer excess (d. e.) were respectively determined by gas chromatography to be 100.0% and 99.4% d. e. $^1$H-NMR spectrum and $^{19}$F-NMR spectrum are shown in the following.

$^1$H-NMR (standard substance: TMS, solvent: DMSO-d$_6$), δ ppm: 1.32(d,6.4 Hz,3H), 1.56(d,6.4 Hz,3H), 3.97(br,3H), 4.45(br,1H), 7.32-7.66(Ar—H,5H).

$^{19}$F-NMR (standard substance: C$_6$F$_6$, solvent: DMSO-d$_6$), δ ppm: 90.78(br-d,3F).

EXAMPLE 6

Hydrogenolysis 1

9.06 g (30.39 mmol, 1.00 eq) of the salt of optically active secondary amine produced in Example 5 (hydrobromide, a twice recrystallized product, chemical purity: 100.0%, diastereomer excess (d. e.): 99.4% d. e.) were neutralized with 50.00 ml (50.00 mmol, 1.65 eq) of 1N sodium hydroxide aqueous solution, followed by extraction two times with 20 ml of ethyl acetate. The recovered organic layer was washed one time with 10 ml of saturated brine, followed by drying with anhydrous sodium sulfate and concentration under reduced pressure, thereby obtaining 7.58 g (partially containing the extraction solvent, theoretical recovery: 6.60 g) of a free base of optically active secondary amine represented by the following formula.

[Chem. 13]

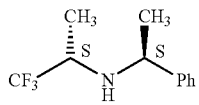

To 30 ml of methanol, there were added 7.58 g (determined as 30.39 mmol) of the total amount of the free base of the optically active secondary amine and 0.33 g (5.0 wt % relative to the theoretical recovery of the optically active secondary amine) of 5% Pd/C (50 wt % wet). The hydrogen pressure was set to 0.5-0.6 MPa, and stirring was conducted at 60-62° C. for 15 hr. The reaction-terminated liquid was subjected to Cellite filtration, followed by washing with 5 ml of methanol. Conversion of the filtrate was determined by gas chromatography to be 100%. 40 ml of 10% methanol hydrochloride were added to the filtrate to have a pH of 1, followed by concentration under reduced pressure, thereby obtaining 2.61 g of crude crystals of a salt of optically active 1-alkyl-substituted 2,2,2-trifluoroethylamine represented by the following formula.

[Chem. 14]

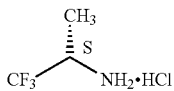

To the distillate upon concentration under reduced pressure, 20 ml of 1N hydrochloric acid aqueous solution were added, followed by concentration under reduced pressure, thereby obtaining 2.85 g of crude crystals of the salt of optically active 1-alkyl-substituted 2,2,2-trifluoroethylamine, which is represented by the above formula. The former is the first crude crystals, and the latter the second crude crystals. 10 ml of toluene were added to 2.61 g of the total amount of the first crude crystals, followed by stirring at room temperature and filtration. The crystals were washed with a small amount of toluene, followed by drying under reduced pressure and vacuum drying, thereby obtaining 1.63 g of the purified crystals (determined as the first purified crystals, yield: 36%, chemical purity by gas chromatography: 99.5%, and enantiomer excess (e. e.): 99.3% e. e.) of the salt of optically active 1-alkyl-substituted 2,2,2-trifluoroethylamine, which is represented by the above formula. 10 ml of toluene were added to 2.85 g of the total amount of the second crude crystals, followed by stirring at room temperature and filtration. The crystals were washed with a small amount of toluene, followed by drying under reduced pressure and vacuum drying, thereby obtaining 0.90 g of the purified crystals (determined as the second purified crystals, yield: 20%, chemical purity by gas chromatography: 99.4%, and enantiomer excess (e. e.): 99.3% e. e.) of the salt of optically active 1-alkyl-substituted 2,2,2-trifluoroethylamine, which is represented by the above formula. The filtrates obtained upon stirring and washing the first crude crystals and the second crude crystals with toluene were combined together, followed by concentration under reduced pressure, thereby obtaining 2.75 g of crude crystals (determined as the third crude crystals) of the salt of optically active 1-alkyl-substituted 2,2,2-trifluoroethylamine, which is represented by the above formula. The quantified value of the third crude crystals according to the internal standard method of $^{19}$F-NMR spectrum was 1.54 g (yield: 34%, chemical purity by gas chromatography: 94.6%, and enantiomer excess (e. e.): 99.1% e. e.).

The total yield of the first purified crystals, the second purified crystals, and the third crude crystals was 90%. Enantiomer excess (e. e.) was determined by chiral gas chromatography, after the salt of optically active 1-alkyl-substituted 2,2,2-trifluoroethylamine was converted into a benzamide derivative using excessive benzoyl chloride and pyridine. $^{1}$H-NMR spectrum and $^{19}$F-NMR spectrum are shown in the following.

$^{1}$H-NMR (standard substance: TMS, solvent: DMSO-d$_6$), δ ppm: 1.37(d,7.2 Hz,3H), 4.24(septet,7.2 Hz,1H), 9.24(br, 3H).

$^{19}$F-NMR(standard substance: C$_6$F$_6$, solvent: DMSO-d$_6$), δ ppm: 88.03(d,7.2 Hz,3F).

EXAMPLE 7

Salt Purification 2

To 10 ml of i-propanol, 2.00 g (9.207 mmol, 1.00 eq, diastereomer excess (d. e.): 42.9% d. e.) of the optically active secondary amine produced similar to Example 2 or Example 4 and 2.14 g (9.212 mmol, 1.00 eq) of (1S)-(+)-10-camphorsulfonic acid were added, followed by dissolution with stirring at 80° C. Furthermore, 3.5 ml of n-heptane were added, followed by cooling to room temperature and stirring for the entire night. The precipitated crystals were filtered. The precipitated crystals were washed with a mixed liquid of i-propanol and n-heptane in small amounts, followed by drying under reduced pressure and vacuum drying, thereby obtaining 2.09 g of a salt of optically active secondary amine represented by the following formula.

[Chem. 15]

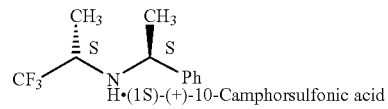

Recovery of the recrystallization purification to S—S configuration was 71%. The product was neutralized with 1N sodium hydroxide aqueous solution, followed by extraction with ethyl acetate. Diastereomer excess (d. e.) was determined by gas chromatography to be 97.3% d. e. $^{1}$H-NMR spectrum and $^{19}$F-NMR spectrum are shown in the following.

$^{1}$H-NMR (standard substance: TMS, solvent: CDCl$_3$), δ ppm: 0.88(s,3H), 1.16(s,3H), 1.44(m,1H), 1.68(d,6.8 Hz,3H), 1.81(m,1H), 1.92(d,19.6 Hz,1H), 1.93(d,6.8 Hz,3H), 2.06(m,1H), 2.10(m,1H), 2.35(dt,18.0 Hz,3.8 Hz,1H), 2.76 (m,1H), 2.87(d,14.8 Hz,1H), 3.40(d,14.8 Hz,1H), 3.41(septet,6.8 Hz,1H), 4.57(q,6.8 Hz,1H), 7.40(Ar—H,3H), 7.60 (Ar—H,2H), It was not possible to assign broad peaks derived from —NH and —SO$_3$H.

$^{19}$F-NMR (standard substance: C$_6$F$_6$, solvent: CDCl$_3$), δ ppm: 91.23(br-d,3F).

The invention claimed is:

1. A process for producing an optically active 1-alkyl-substituted 2,2,2-trifluoroethylamine represented by the formula [3],

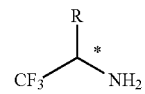

[3]

wherein
R represents a lower alkyl group of a carbon number of 1 to 6, and
* represents an asymmetric carbon, or its salt by subjecting an optically active imine represented by the formula [1],

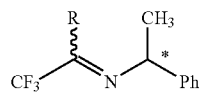

wherein
R represents a lower alkyl group of a carbon number of 1 to 6,
Ph represents a phenyl group,
a wavy line represents E configuration or Z configuration, and
* represents an asymmetric carbon, to an asymmetric reduction under hydrogen atmosphere using a metal catalyst of Group VIII to convert it into an optically active secondary amine represented by the formula [2],

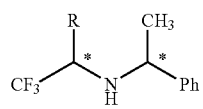

wherein
R represents a lower alkyl group of a carbon number of 1 to 6,
Ph represents a phenyl group, and
* represents an asymmetric carbon, and then by subjecting the secondary amine or its salt to hydrogenolysis.

2. A production process according to claim 1, wherein the asymmetric reduction is conducted under a temperature condition of not higher than 10° C.

3. A production process according to claim 1, wherein R of the optically active imine represented by the formula [1], the optically active secondary amine represented by the formula [2] and the optically active 1-alkyl-substituted 2,2,2-trifluoroethylamine represented by the formula [3] is a methyl group.

4. A production process according to claim 1, wherein the optically active imine represented by the formula [1] is an optically active imine obtained by subjecting
a trifluoromethyl alkyl ketone represented by the formula [4]

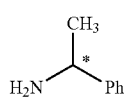

wherein
R represents a lower alkyl group of a carbon number of 1 to 6, and an optically active 1-phenylethylamine represented by the formula [5]

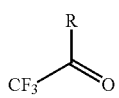

wherein
Ph represents a phenyl group, and
* represents an asymmetric carbon, to dehydration and condensation in the presence of an acid catalyst.

5. A purification process characterized in that an optically active secondary amine represented by the formula [2]

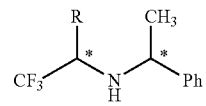

wherein
R represents a lower alkyl group of a carbon number of 1 to 6,
Ph represents a phenyl group, and
* represents an asymmetric carbon, is converted into its salt, followed by a recrystallization purification.

6. A purification process according to claim 5, wherein R of the optically active secondary amine represented by the formula [2] is a methyl group, and the salt is a, hydrobromide.

7. A purification process according to claim 5, wherein R of the optically active secondary amine represented by the formula [2] is a methyl group, and the salt is an optically active 10-camphorsulfonate.

8. A process for producing an optically active 1-alkyl-substituted 2,2,2-trifluoroethylamine represented by the formula [3] or its salt, according to claim 1, which is characterized in that, after an optically active secondary amine represented by the formula [2] is obtained by a production process according to claim 1, the secondary amine is purified by converting the secondary amine into its salt, followed by a recrystallization purification.

9. An optically active secondary amine represented by the formula [2]

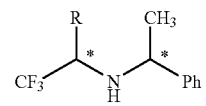

wherein
R represents a lower alkyl group of a carbon number of 1 to 6,
Ph represents a phenyl group, and
* represents an asymmetric carbon, or a salt thereof.

10. An optically active secondary amine according to claim 9, wherein R of the optically active secondary amine represented by the formula [2] is a methyl group.

11. A hydrobromide of the optically active secondary amine according to claim 9, wherein R of the optically active secondary amine represented by the formula [2] is a methyl group.

12. An optically active 1-camphorsulfonate of the optically active secondary amine according to claim 9, wherein R of the optically active secondary amine represented by the formula [2] is a methyl group.

* * * * *